United States Patent [19]

Spencer et al.

[11] Patent Number: 5,156,701
[45] Date of Patent: Oct. 20, 1992

[54] TOTAL CONTAINMENT WELDING OF PLASTIC TUBES

[75] Inventors: Dudley W. C. Spencer; John B. Shaposka, both of Wilmington, Del.

[73] Assignee: Denco Inc., Wilmington, Del.

[21] Appl. No.: 682,977

[22] Filed: Apr. 10, 1991

Related U.S. Application Data

[63] Continuation-in-part of Ser. No. 604,979, Oct. 29, 1990, which is a continuation-in-part of Ser. No. 569,855, Aug. 20, 1990.

[51] Int. Cl.$^5$ .................... B29C 65/20; A61M 5/00
[52] U.S. Cl. ......................... 156/158; 156/159; 156/251; 156/258; 156/304.2; 156/304.5; 156/304.6; 156/515; 156/518; 156/530
[58] Field of Search ............... 156/158, 304.2, 304.5, 156/304.6, 251, 258, 515, 518, 530

[56] References Cited

U.S. PATENT DOCUMENTS

| | | | |
|---|---|---|---|
| 3,968,195 | 7/1976 | Bishop | 156/304.2 |
| 4,737,214 | 4/1988 | Leurink et al. | 156/158 |
| 4,753,697 | 6/1988 | Shapuska et al. | 156/304.2 |

Primary Examiner—Caleb Weston
Attorney, Agent, or Firm—Connolly & Hutz

[57] ABSTRACT

Plastic tubes are welded together by placing each tube in a nest which includes a pair of grooves and an anvil centrally located between the grooves. Each tube is positioned in the grooves around the anvil for being juxtaposed the other tube. A wafer of movably mounted to move to the gap between the anvils so as to heat the ends of the tubes and melt the tubes without actually cutting through the tubes. The melted ends are then joined together so that the two tubes are thereby connected with one section of each tube being in flow communication with a corresponding section of the other tube.

45 Claims, 8 Drawing Sheets

Initial State     *Fig. 17A.*

Bio-Reactor

First Sample     *Fig. 17B.*

Closing System     *Fig. 17C.*

Next Sample     *Fig. 17D.*

Fig. 18A.
_Initial State_

Bio-Reactor

Fig. 18B.
_First Sample_

Fig. 18C.
_Next Sample_

_Repeat Above Step For Rest Of Sample_

Fig. 18D.
_To Close The System After n Samples_

Fig. 19A.

Initial State

Fig. 19B.

Re-Installing Bag For Next Exchange

Fig. 19C.

Bag Exchange

Fig. 19D.

Bagging-Off

_Initial State_    _Fig. 20A._

_Loading_    _Fig. 20B._

_Fig. 20C._
_After Welding_

TOTAL CONTAINMENT WELDING OF PLASTIC TUBES

Cross-Reference to Related Application

This application is a continuation-in-part of application Ser. No. 07/604,979 filed Oct. 29, 1990. That application in turn is a continuation-in-part of application Ser. No. 07/569,855 filed Aug. 20, 1990.

BACKGROUND OF THE INVENTION

The present invention relates to the sterile and total containment welding techniques for fluid filled plastic tubes. There are many applications which require a plastic tube to be connected to another plastic tube. Such applications include, for example, the taking of samples from a bioreactor, the treating of blood, CAPD and other medical applications. Prior patents generally dealing with this subject include U.S. Pat. Nos. 4,793,880; 4,610,670; 4,369,779; and 4,753,697.

SUMMARY OF THE INVENTION

An object of this invention is to provide a total containment welding system for plastic tubes.

A further object of this invention is to provide such a welding system which could be conveniently manipulated to insert and remove the tubes.

In accordance with this invention a nest is provided for each tube. The nest is in the form of a block member having a pair of side by side parallel tube receiving areas with an anvil located forward of and between the areas. Each tube is mounted in the areas by being bent around the anvil. The nests are located with respect to each other so that the bent ends of the tubes make slight touching contact or are slightly spaced from each other by a gap of such a size that a heated wafer may move therebetween thus causing the bent ends of the tubes to melt and later be joined together after the wafer has passed through.

In one embodiment of this invention the nests are mounted directly on a wafer applicating instrument by being disposed in a channel in the instrument.

The outer sides of the nests may have clamp members located thereat to press against the tubes in the vicinity of the anvil. In one embodiment of the invention one of the clamp members is pivotally mounted as is the nest itself to provide better access for fitting the tube in the tube receiving areas. In an alternative embodiment of the invention both clamp arms are pivotally mounted and the nest could be fixedly mounted. The tube may be prepackaged in a nest in a sealed packet so as to be maintained in a sterilized condition.

The Drawings

FIGS. 21A-21C are top plan views showing the practice of the invention in installing a consumable reagent or the like;

Detailed Description

Figures 1, 2, 3, 4, 5, 6, 7:
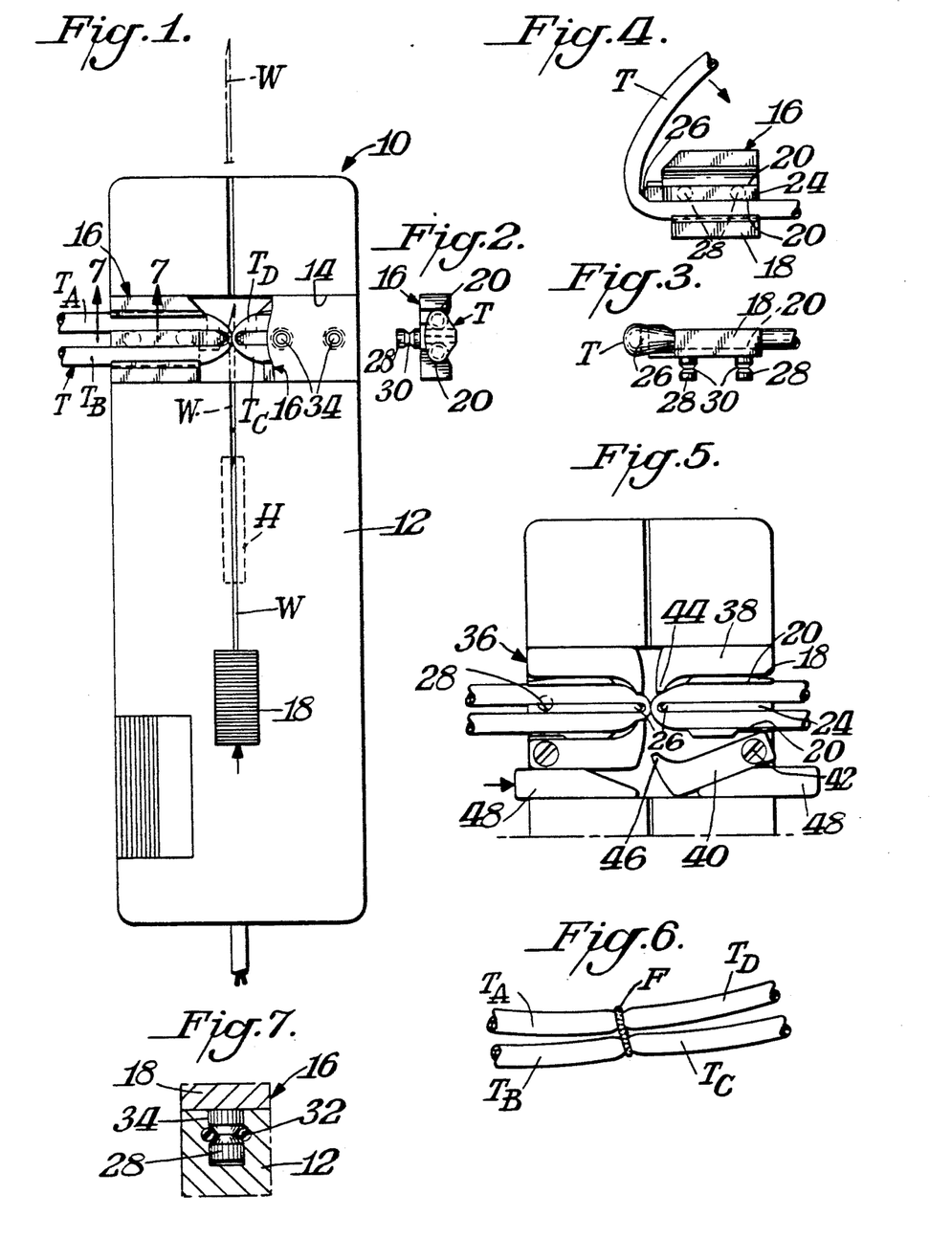
FIG. 1 is a top plan view of a total containment welding system in accordance with this invention.
FIG. 2 is an end elevational view of the nest used in the system of FIG. 1.
FIG. 3 is a side elevational view of the nest shown in FIG. 2.
FIG. 4 is a top plan view showing a step in the insertion of a tube in the nest of FIGS. 2-3.
FIG. 5 is a top plan view of a modified nest in accordance with this invention.
FIG. 6 is a side elevational view of a pair of tubes welded together in accordance with this invention.
FIG. 7 is a cross-sectional view taken through FIG. 1 along the line 7—7.

FIG. 1 illustrates a total containment welding system 10 which includes a holder 12 having a channel 14 across one end. A pair of nests 16 are fixedly mounted in the channel disposed toward each other. It is to be understood that the particular holder 12 is shown and described herein for illustrative purposes only and that the invention may be practiced by any arrangement which includes some means for mounting a pair of nests 16,16 in a fixed relationship with each other and for moving a heated wafer through the junction or slight gap formed by the bent tubes so as to perform a melt-/wipe operation. In the broad practice of the invention, the tubes may be cut by the wafer and one of the nests may be slidable toward the other nest to perform the welding of the tubes with each other. Such mounting of tube holders which are slidable relative to each other is known in the art. The known tube holders, however, do not include the nest structure of this invention. The invention is preferably practiced by the melt/wipe operation described in parent application Ser. No. 07/604,979.

Each nest 16 is best illustrated in FIG. 4. As shown therein the nest is in the form of a metal block 18 having a pair of tube receiving areas in the form of grooves 20 of arcuate shape for snuggly receiving the tube T. Each nest is provided with a partition or separating wall 24 which terminates at its forward end in a pointed anvil 26. Anvil 26 is disposed at least at the edge of block 18 and preferably beyond the outer edge to assure that block 18 does not interfere with the sliding wafer W. The lower surface of block 18 includes a pair of locking pins 28 provided with a peripheral groove 30 for snapping into a corresponding hole in the holder 12. FIG. 7, for example, illustrates holder 12 to include a resilient O-ring 32 in each hole 34. When the pin 28 is snapped into hole 34 the O-ring 32 fits around groove 30 to firmly hold nest 16 in its proper position in channel 14 of holder 12.

In practice, before nest 16 is assembled onto holder 12 a tube T is inserted in one groove 20 of nest 16 and the tube is then bent around anvil 26 with the pointed end and sloping surfaces of the anvil causing a flattening of the tube at the bent portion. The other portion of the tube is then inserted in the other groove 20. Both grooves 20,20 are side by side and parallel to each other. After the tube T has been mounted in nest 16, the assembly of the tube and nest is then mounted in channel 14 of holder 12 so that the pair of tubes are juxtaposed each other making slight contact or having a slight gap therebetween. The wafer W moves through heater H and then through the junction or gap to separate the two tubes into four sections $T_A$, $T_B$, $T_C$, and $T_D$. Initially $T_A$ and $T_B$ form part of the same tube while $T_C$ and $T_D$ form part of the other tube. After the wafer has passed through the junction to perform the melt/wipe operation the sections become joined with $T_A$ being connected with $T_D$ and $T_B$ being connected to $T_C$. A weld seam flange F joins all four sections together as illustrated in FIG. 6. Eventually the weld seam is broken so that the new tubes formed by the newly formed sections can be separated from each other.

The invention may be practiced with disposable nests by using a suitable plastic material. Where the anvil 28 itself is plastic, the melting can take place over an area from the flat portion of the partition 24 including melting the tubes and the plastic anvils.

FIG. 5 illustrates a modified form of this invention wherein a pair of nests 36 are mounted in channel 14. Nests 36 also include the pair of grooves 20,20 and the separating wall or partition 24 which terminates in an anvil 26. Nest 36, however, differs from nest 16 in that a pair of clamp arms 38,40 are provided alongside each groove. In the embodiment of FIG. 5, clamp arm 36 is fixedly mounted so that its bent end 44 is only slightly spaced from anvil 26 in the operative position of nests 36. Clamp arm 40, however, is pivotally mounted by being secured to pivot pin 42. A further difference between nest 36 and nest 16 is that only a single pin 28 secures the nest in channel 14 for nest 36. As a result, the entire nest 36 may pivot within the limits provided by its abutment with fixed arm 38.

In the practice of the embodiment of FIG. 5, when it is desired to insert a tube in nest 36 arm 40 is pivoted away from block 18. Block 18 would then be rotated toward the open arm 40 thereby moving anvil 26 away from the curved end 44 of fixed arm 38. This pivotal movement thereby maximizes the spacing between curved end 44 and anvil 26 to permit the tube T to be inserted in its groove 20 adjacent fixed arm 38. The tube would be bent around anvil 26 while the block 18 is still in its pivoted position because of the access provided by the curved end 46 of pivoted clamp arm 40 being disposed away from anvil 26.

In the illustrated practice of this invention clamp arms 38,40 are permanently mounted in channel 14 of holder 12 with the nest 36 being detachably mounted in channel 14. It is to be understood, however, that the invention may also be practiced by mounting the clamp arms 38 and 40 to a common support with nest 36 wherein the resulting assembly and support itself would then be secured in channel 14.

An alternative manner of mounting the tubes, which is the preferred practice for nests 36, would be to premount the tubes on the nests 36 before the nests are secured in channel 14. In this arrangement, when the nests are then mounted in channel 14, the arms 40 would be pivoted away from the nests and the nest block 18 would be pivoted toward the movable clamp arm 40 to provide the sufficient clearance between end 44 of fixed arm 38 and anvil 26.

After the nest and its mounted tubes have been secured in channel 14 it is necessary to close movable clamp arms 40. This is accomplished by sliding a wedge member 48 into the space between the movable clamp arm 40 and the corresponding wall of channel 14. FIG. 5, for example, illustrates one of the wedge blocks 48 on the left hand side to be fully inserted so as to hold its clamp arm 40 in the clamped condition whereby the tube T is flattened around anvil 26. FIG. 5 also illustrates the initial stage of inserting wedge block 48 against clamp arm 40 in the right hand portion of FIG. 5. As is apparent, the sliding of wedge block 48 causes arm 40 to pivot to its straight position which in turn causes nest 36 to be pivoted to its straight position.

Figures 8, 9, 10, 11, 12, 13, 14, 15, 16:
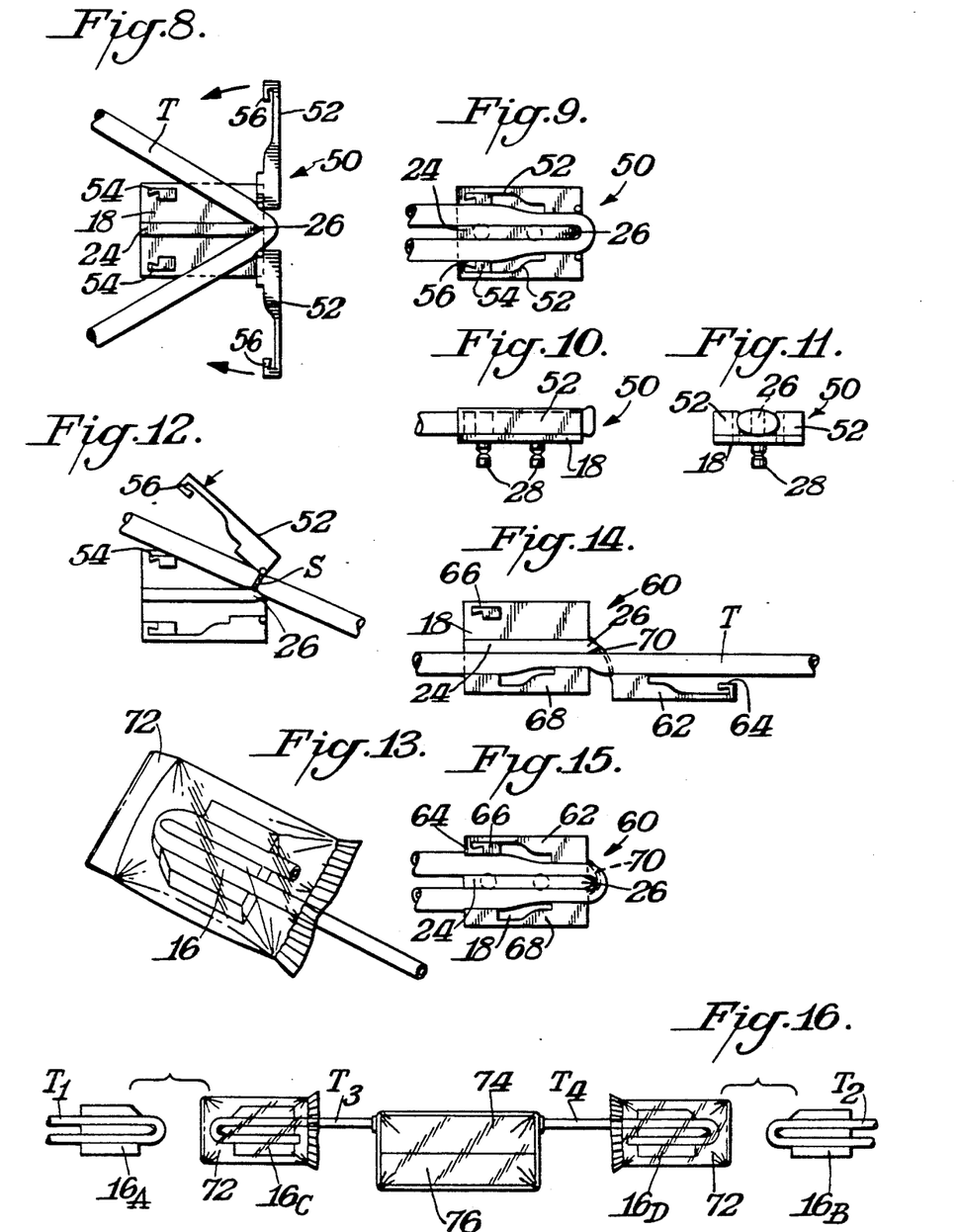
FIG. 8 is a top plan view of a further form of nest in accordance with this invention.
FIG. 9 is a top plan view of the nest shown in FIG. 8 with the arms in their closed position.
FIG. 10 is a side elevational view of the nest shown in FIGS. 8-9.
FIG. 11 is an end elevational view of the nests shown in FIGS. 8-10.
FIG. 12 is a top plan view showing a method of using the nest of FIGS. 8-11 for breaking the weld seam flange that holds two joined tubes together.
FIG. 13 is a perspective view of a nest of the type shown in FIG. 1 mounted in a sealed packet.
FIG. 14 is a top plan view of a further nest in accordance with this invention.
FIG. 15 is a top plan view of the nest shown in FIG. 14 in its closed condition.
FIG. 16 is a top plan view schematically showing one application in the practice of this invention.

FIGS. 8-11 illustrate a further embodiment of this invention wherein the nest 50 is provided with a pair of pivoted resilient clamp arms 52,52. As with the prior embodiments, nest 50 includes the block 18 having the central partition 24 which terminates in an anvil 26. This embodiment illustrates that the provision of tube receiving areas in the form of physical grooves to hold the bent tube in place is not actually necessary. Thus, for example, partition 24 may have straight walls and the top surface of block 18 may be straight. The tube would still be held in its proper position by being clamped between partition 24 and a corresponding clamp arm 52. If desired, shallow grooves may be formed in the upper surface of block 18 or grooves may be formed in the side walls of partition 24 and the corresponding flat portions of clamp arms 52. Block 18 also includes a pair of fixed lock members 54 which extend upwardly away from the top surface of block 18. Each clamp arm 52 is also provided with a complementary locking structure 56 which engages locking members 54 when the clamping arms 52 are moved to their closed positions as shown in FIG. 9. The clamping arms 52 are unlocked by pressing the arms at their thin portions near the locking structures to bend the arm inwardly and snap its locking structure away from the locking structure of member 54.

FIG. 8 illustrates the advantage of nest 50 in that it provides access around anvil 26 for facilitating the mounting of the tube in a bent fashion on nest 50.

FIG. 12 illustrates a further advantage of this invention wherein a movable clamp arm is used. As shown therein, the tube T which has been welded together in the manner illustrated in FIG. 6 is inverted so that, for example, the joined sections $T_A$ and $T_D$ are mounted above joined sections $T_B$ and $T_C$. When in this position the joined tube sections $T_B$ and $T_C$ are disposed in nest 50 with the seam flange F being located at anvil 26. The corresponding arm 52 is then moved to a closed position as shown by the arrow and this closing movement causes the seam F to sever so that the joined sections $T_A$ and $T_D$ are separated from the remaining joined sections $T_B$ and $T_C$. The various pivoted clamp arms in the different embodiments could also be used as pliers to open communication of joined sections.

FIGS. 14–15 illustrate a further embodiment of this invention wherein the nest 60 includes a single pivoted clamp arm 62 having locking structure 64 which engages locking structure 66 on block 18. A fixed clamp arm 68 is provided on the other portion of block 18. Movable clamp arm is connected to block 18 by a flexible hinge 70 which is disposed below anvil 26. The flexible hinge permits clamp arm 62 to be moved a sufficient distance away from block 18 so that a tube T can be placed between partition 24 and fixed clamp 68 while the tube is still in a straight condition as illustrated in FIG. 14. Arm 62 may be moved at least in line with and preferably beyond clamp 68. The tube would then be bent around anvil 26 against the opposite side of partition 24. This manipulation is again done while there is minimal obstruction because clamp arm 62 is located in its remote position. After the tube T has been bent around anvil 26, clamp arm 62 is closed and locked in position by engagement of locking members 64 and 66 to clamp one section of the tube between clamp arm 62 and partition 64 with the other section being clamped between stationary clamp member 68 and partition 24 as illustrated in FIG. 15. The embodiment of nest 60 is particularly advantageous for use by people with impaired eyesight, including blind people or people having limited dexterity since it maximizes the open area and minimizes the number of manipulations necessary for the mounting of the tube in nest 60.

FIG. 13 illustrates an advantageous feature of this invention wherein a tube is premounted in a nest, such as nest 16 and the premounted end of the tube and its nest are packaged in a sterile envelope 72. This assures maintaining the tube end in a sterile condition until it is time for actual mounting of the nest on the holder. The use of a sterile package is particularly desirable when the tube terminates in an open end rather than terminating in a factory made hematron type seal.

FIG. 16 illustrates one application of the invention for use, for example, in blood sampling or processing. In the illustrated embodiment a tube $T_1$ would be mounted in a nest $16_A$. It is intended to have flow communication between tube $T_1$ and tube $T_2$. Accordingly, tube $t_2$ would be mounted in nest $16_B$. A pair of prepackaged nests $16_C$ and $16_D$ would be provided having their tubes $T_3$ and $T_4$ communicating with a bag or container 74. The ends of tube $T_3$ and $T_4$ might be initially packaged in sterilzed packet 72. The pair of nests $16_A$ and $16_C$ are mounted in the same holder to connect sections of tubes $T_1$ and $T_3$ while nests $16_B$ and $16_D$ are mounted in the same holder to connect sections of tubes $T_2$ and $T_4$. After such connection has been made, a partition in bag 74 is broken so that the blood or other fluid may mix with fluid in the partitioned bag 74 on the side 76 of the partition remote from the portion of the bag which is connected to tubes $T_3$ and $T_4$. Alternatively, bag 74 may include capsules which could be broken by a squeezing to introduce some form of reagent, etc. into the blood or other fluid flowing through the tubes.

It is to be understood that while FIG. 16 illustrates the nest to be in the form of nest 16 the other forms of nest herein may be used. Similarly, FIGS. 17-22 illustrate various practices of the invention which may include any form of nests described herein.

Figure 17A:
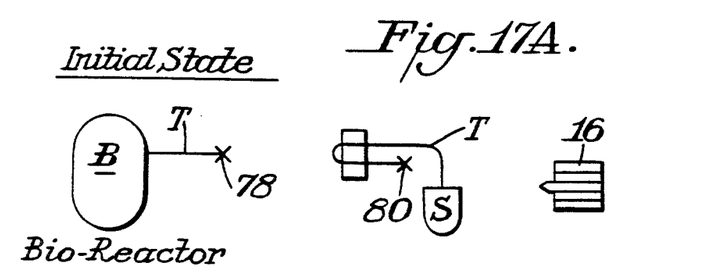
FIGS. 17A-17D are top plan views showing the application of this invention for the taking of samples with intermediate sealing.
Figure 17B:
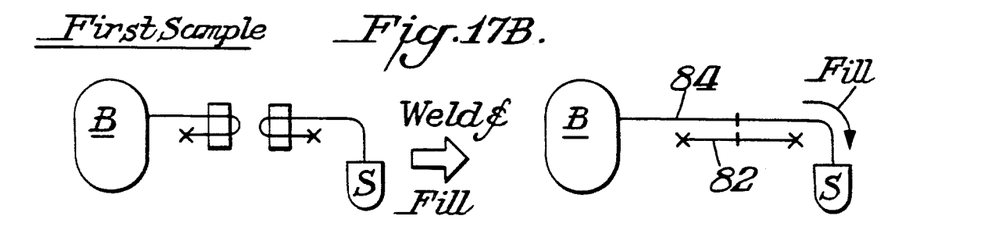

FIGS. 17A–17B illustrate the practice of the invention for use in the taking of samples with intermediate sealing. As shown therein, a bioreactor B is provided having a tube T with a sealed end 78. It is desired to connect bioreactor B with sample S. Sample S in turn includes a tube T having a sealed end 80. In general, the invention is practiced by providing a presealed package 72 whenever the tube end is not hemotron closed. Conversely, where the tube end is hematron closed the prepackaging is not necessary. In FIGS. 17-22 an "X" is used to designate the sealed end of a tube.

FIG. 17A illustrates the general arrangement before bioreactor B is connected to sample S which contains various consummables. FIG. 17B illustrates the arrangement for the taking of a first sample. As shown therein, the tube T leading from bioreactor B is mounted in a nest 16 juxtaposed the tube T from sample S. After the tube sections have been connected together a stub 82 results with the other tube sections being connected together to form a single main tube 84. Material from bioreactor B then flows into sample S to fill the sample.

Figure 17C:
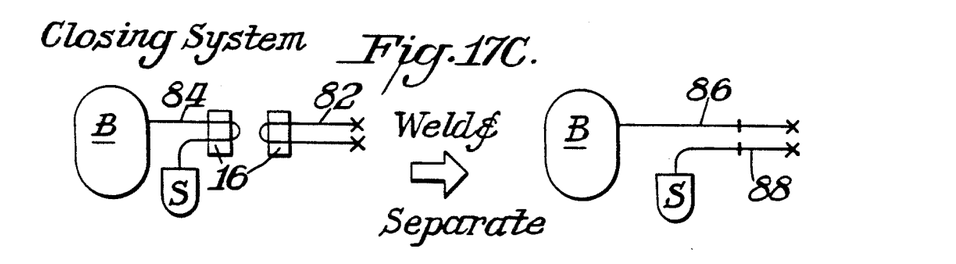

FIG. 17C shows the steps in the closing of the system. As shown therein, after the sample S has been filled the tube 84 is mounted in a nest 16 and the stub 82 is mounted in a corresponding nest 16. By use of the melt/wipe operation, a new tube 86 results formed from a portion of tube 84 and a portion of tube stub 82 which leads from bioreactor B. Similarly, a tube 88 is formed which communicates with sample S. The two new tubes are sealed. The sample S can then be refrigerated, assayed, etc. while the bioreactor remains sealed.

Figure 17D:
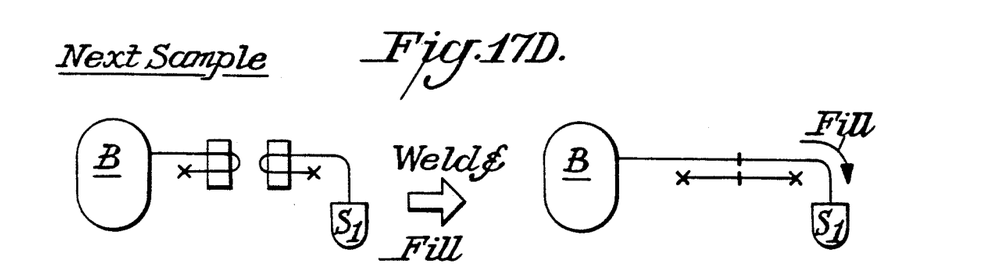

FIG. 17D illustrates how a further sample $S_1$ could be taken in a manner similar to the taking of sample S.

Figure 18A:
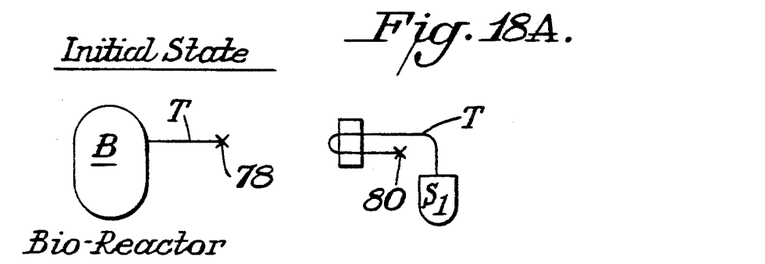
FIGS. 18A-18D are top plan views showing the taking of continuous samples in accordance with this invention.
Figure 18B:
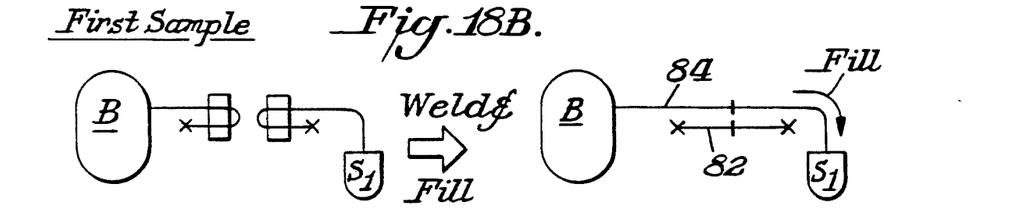
Figure 18C:
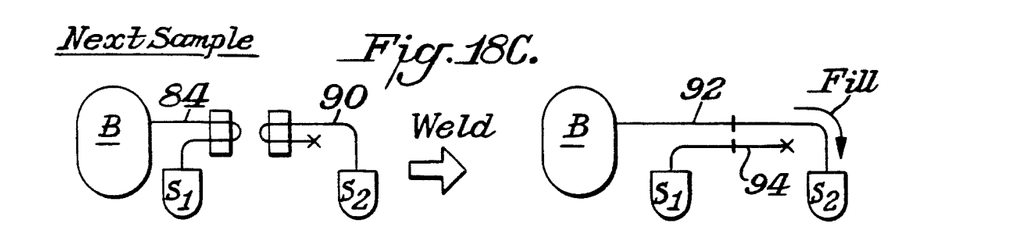
Figure 18D:
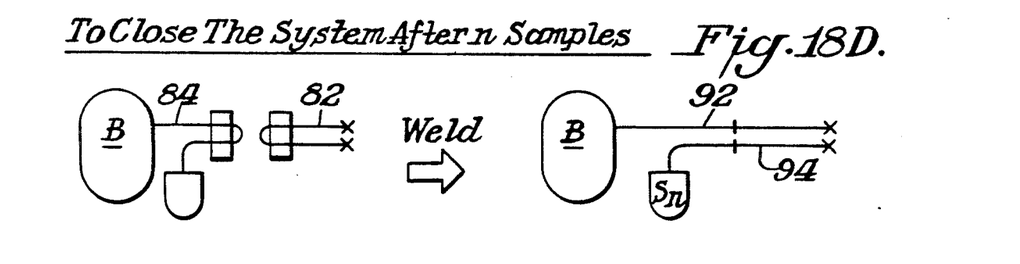

FIGS. 18A–18D illustrate the practice of this invention for continuous sampling. FIG. 18 A shows the initial state which is the same as FIG. 17A. Similarly, FIG. 18B illustrates the formation of a tube 84 and a stub 82 similar to FIG. 17B. FIG. 18C, however, illustrates the steps for taking the next sample $S_2$. As shown therein, a portion of the tube 84 is joined to a portion of tube 90. The result is, the formation of a new tube 92 which communicates the bioreactor B with sample $S_2$ until $S_2$ is filled. The first sample $S_1$ is separated with its tube 94. The above steps would be repeated for taking any number of samples up to sample $S_n$. FIG. 18 D illustrates the steps for closing the system after n number of samples has been taken. As shown therein tube 84 is to be connected to stub 82 which would have been left over from, for example, the taking of the first sample or could comprise a new tube section. After that operation a new tube 92 is formed which has a sealed end and leads from bioreactor B while the last sample $S_n$ has its tube 94.

Figure 19A:
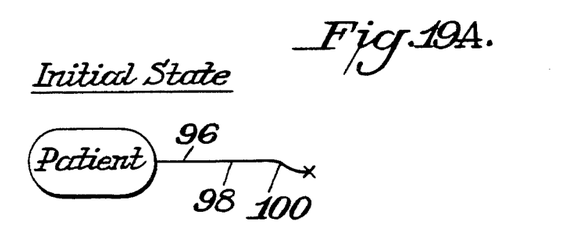
FIGS. 19A-19D are top plan views showing the application of this invention for CAPD application.
Figure 19B:
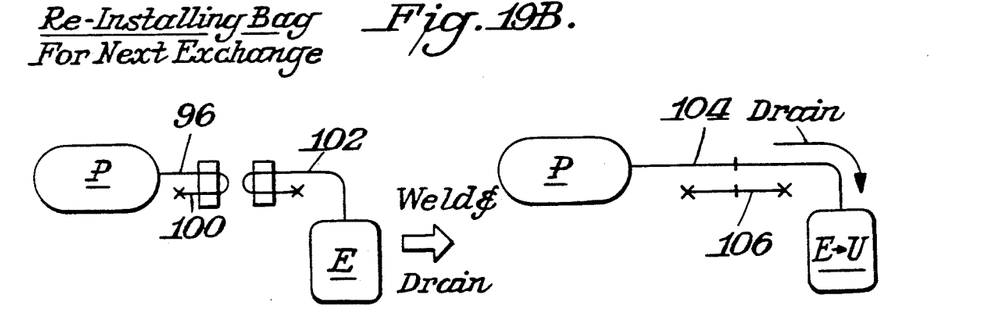
Figure 19C:
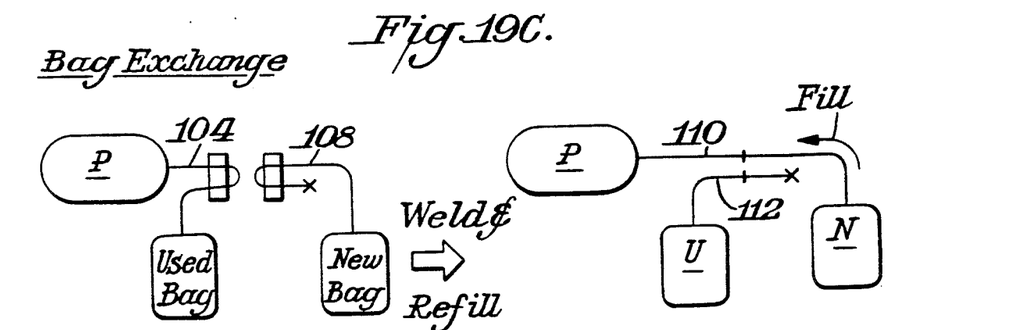

FIGS. 19A–19C illustrate the practice of the invention for use in CAPD with bag-off. As shown therein, the patient P would have a tube 96 and might, for example, have joined thereto at weld 98 a second tube 100 having a factory made hematron seal. It is intended to reinstall a bag for the next exchange. This is accomplished by providing an empty bag E having its tube 102 positioned in a nest with the tube 96,100 positioned in a corresponding nest. After the melt/wipe operation and a draining operation the patient is connected by the newly formed tube 104 with the bag E and a stub 106 remains which is later used for the bag-off operation.

FIG. 19C illustrates the steps for a bag exchange. As shown therein, the patient has the tube 104 connected to the used bag U while the new bag N has its tube 108. Each tube is placed in the corresponding nest and the tubes are connected to each other so that the patient is connected to the new bag N by resulting tube 110 while the used bag U has its tube 112. The used bag is capped and discarded.

Figure 19D:
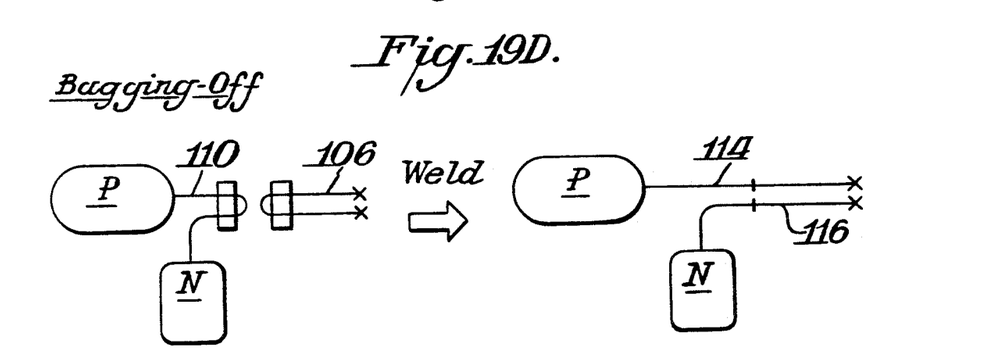

FIG. 19D illustrates the bagging-off operation wherein the stub 106 which had previously been formed is mounted in a nest associated with the nest for tube 110. After the wipe/melt operation the patient has a resulting tube 114 which is sealed at its end with the now empty new bag end having its tube 116 which again would be sealed.

Figure 20A:
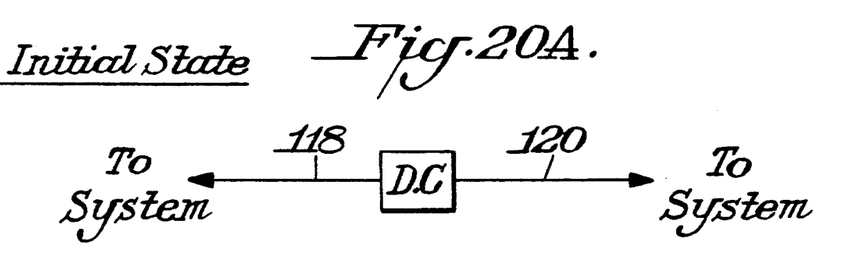
FIGS. 20A-20C are top plan views showing the practice of this invention for removing a sample ring or a depleted consummable.
Figure 20B:
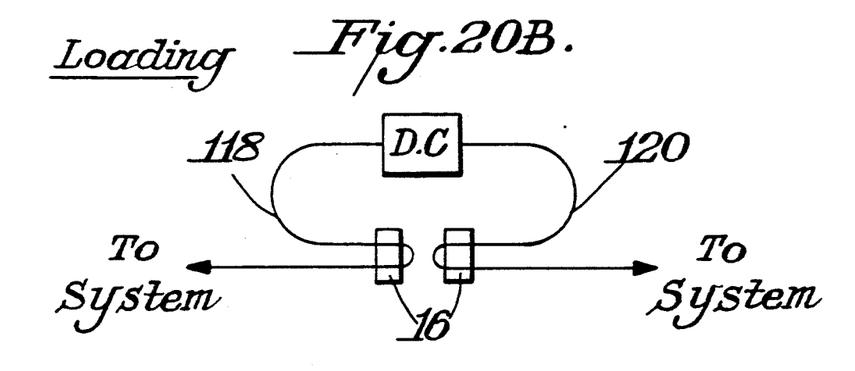
Figure 20C:
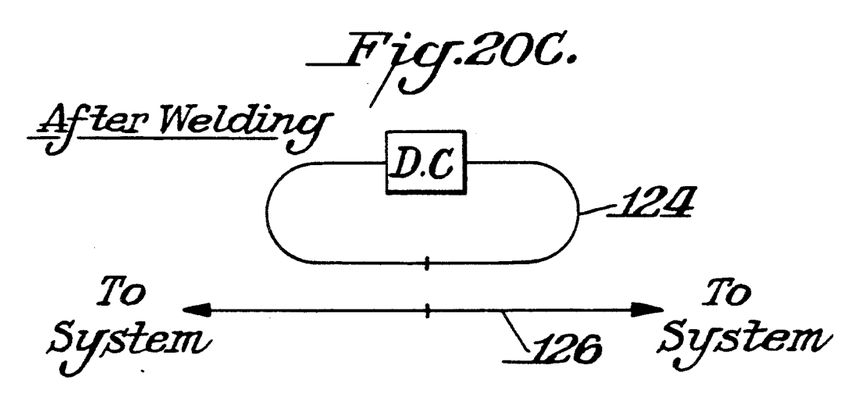

FIGS. 20A-20C illustrate the practice of the invention for removing a sample ring or depleted consummable. FIG. 20A illustrates the initial state where the depleted consummable DC has a pair of tubes 118,120 extending therefrom. FIG. 20B illustrates the loading operation wherein tube 118 is mounted in a nest while tube 120 is mounted in a corresponding nest. The welding operation is then performed and FIG. 20C illustrates the depleted consummable to have a closed loop tube 124 resulting from the welding operation while a tube formed from tube 126 results from sections of tubes 118 and 120.

Figure 21A:
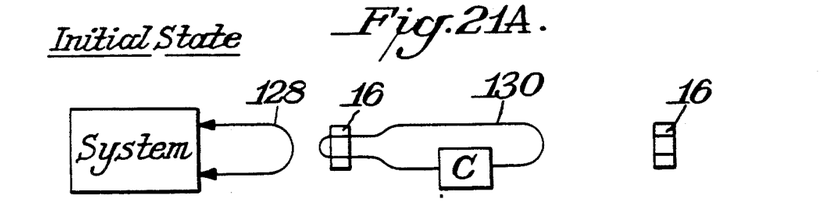
Figure 21B:
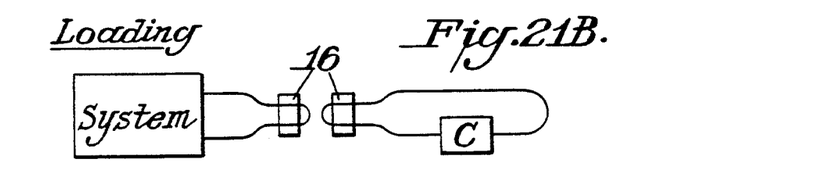
Figure 21C:
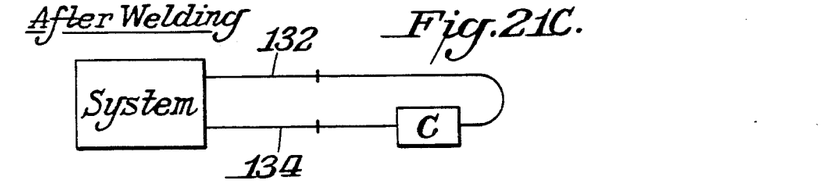

FIGS. 21A-21C illustrate the practice of the invention for installing a consummable reagent, filter pack etc. As shown in FIG. 21A, in the initial state, a tube 128 is provided in closed form connecting with the system. The consummable C which is to be installed is similarily provided with its closed tube 130. Both tubes 128 and 130 are then loaded in nests 16,16 as shown in FIG. 21B. The result illustrated in FIG. 21C is the formation of a tube 132 which extends from the system to consummable C with a second tube 134 extending from consummable C back to the system. The resulting stubs could be discarded.

Figure 22A:
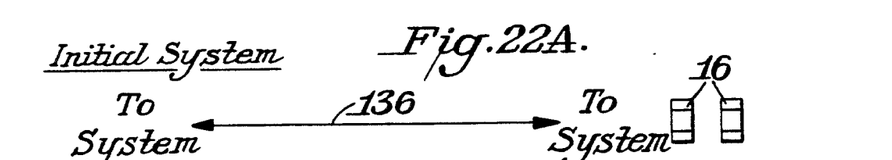
FIGS. 22A-22D are top plan views showing the practice of the invention for tube sealing without separation.
Figure 22B:
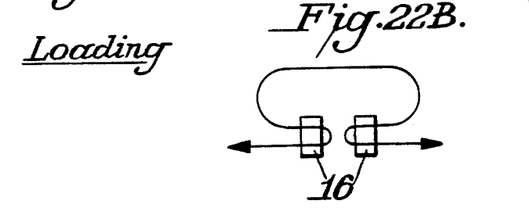
Figure 22C:
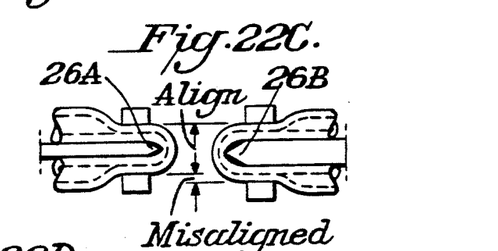
Figure 22D:
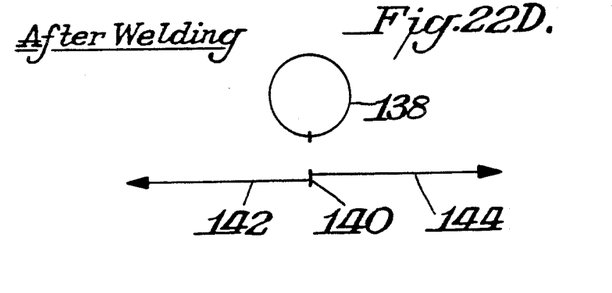

FIGS. 22A-22D illustrate the practice of the invention for tube sealing without separation. FIG. 22A illustrates the initial system wherein a tube 136 is provided which would be connected to two different parts of the system. The tube would be mounted in a pair of nests 16,16 as shown in FIG. 22B. In accordance with the practices described in parent application 07/604,979 one tube section from each tube is aligned with each other while the other tube sections are misaligned. This could be accomplished by having anvil 26B thicker than anvil 26A. As a result, the tube around anvil 26B would have its bent sections spaced further apart than the sections bent around anvil 26A. One set of sections would be aligned, while the other set would contact in mis-alignment. See FIG. 22C. The result after the welding operation is illustrated in FIG. 22D wherein a closed loop 138 results along with a misaligned weld 140 which functions to both seal and connect the tube sections 142,144.

The present invention thus provides various nest structures which may be utilized for joining tube sections. The embodiments range from a fixed nest which could be permanently mounted to a holder and which would represent the most economical version of the invention to a self-loading nest that is detachably mounted to the holder and to a preloaded, prepositioned tube which permits loading by an individual having impaired eyesight or limited dexterity.

The invention may be practiced by having all of the welded tube sections temporarily closed and then selectively opened by placing the tubes which are to be opened in one side of the nest. During the closing action on that side of the nest the clamp arm acts as a pliers to open the joined tubes. Accordingly, one or both joined tubes sections may be opened. Advantageously, the nest also provides a ready means for breaking the seal flange which secures the two newly formed tubes together so that the tubes can be separated. The invention permits tubes to be joined in this manner for a wide variety of applications, only some of which have been illustrated and described for exemplary purposes.

Figure 23:
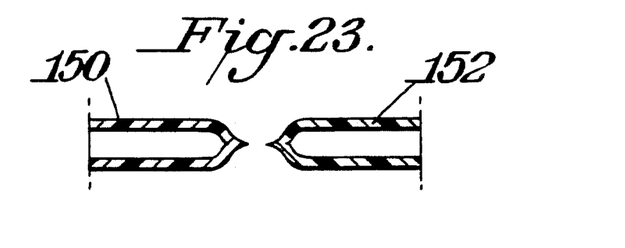
FIGS. 23-27 are schematic views illustrating a variation in the practice of this invention for sealing two distal tube ends.
Figure 24:
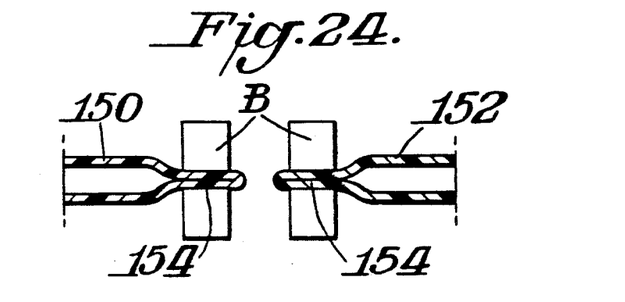
Figure 25:
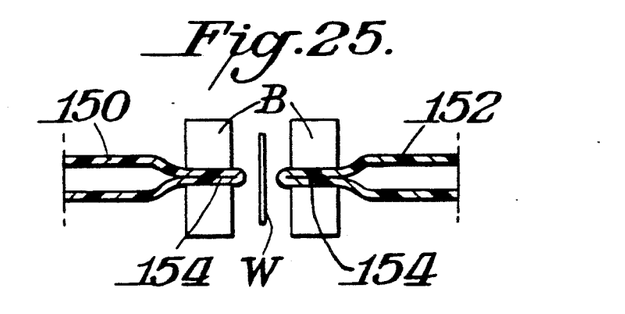
Figure 26:
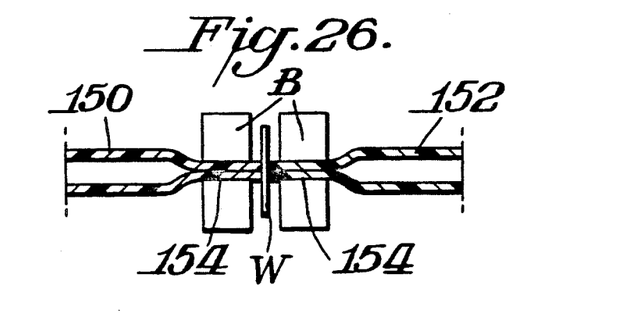
Figure 27:
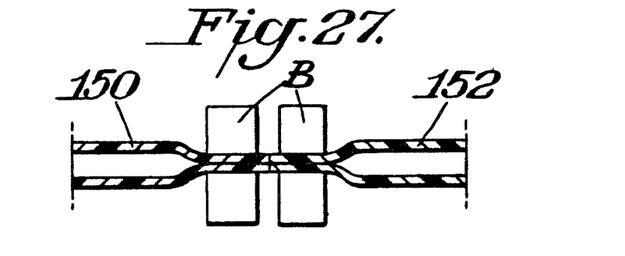

While the invention has been particularly described with respect to using various nest structures, particularly employing the melt/wipe techniques of parent application 07/604,979 the invention may be practiced in other manners. FIGS. 23-27 illustrate a variation in the practice of the invention for providing a sterile seal of two distal tube ends. FIG. 23 illustrates two such tube ends 150,152. As shown in FIG. 24, the tubes 150,152 are placed in coaxial mounting blocks B and clamped. This is done without bending. Accordingly, it is not necessary to use a nest having an anvil, as previously described. The clamping results in flattened portions 154 for each tube 150,152. FIG. 25 illustrates the next step in the sequence wherein a heater, such as wafer W is moved between the tube ends and using the principles of melt/wipe of the parent application the tubes are moved into contact with the heater for accomplishing the melt/wipe step as shown in FIG. 26. The heater is then removed and a joint results which is illustrated in FIG. 27. The tubes may later be reopened in a convenational manner. This practice of the invention would have particularly utility for the factory assembly of tube harnesses, in bio-tech labs, in chemistry labs and for rejoining CAPD patient bags after a bagging off operation.

What is claimed is:

1. A nest for use in the welding of plastic tubes comprising a block having an upper surface, a pair of side by side parallel longitudinal tube receiving areas on said upper surface, an upstanding partition on said upper surface separating said tube receiving areas from each other, said partition terminating at its forward end in an anvil, and said anvil extending to at least the edge of said upper surface whereby a tube may be bent around said anvil with sections of the tube in said tube receiving areas and with the bent portion of the tube extending beyond said upper surface whereby the bent portion of the tube may be contacted by a heated wafer movable beyond said upper surface to permit the tube to be welded to another tube.

2. The nest of claim 1 wherein said anvil terminates in a pointed tip.

3. The nest of claim 2 including at least one locking member extending downwardly from said block for engagement with a support surface whereby said nest is locked to the support surface, and said anvil extending beyond said edge of said upper surface of said block.

4. The nest of claim 1 wherein said anvil is made of a meltable plastic material.

5. The nest of claim 2, in combination therewith, a holder, said holder having an upper surface and said nest being mounted to said upper surface, said nest being a first nest, a second nest disposed in line with an adjacent to said first nest, said second nest having an anvil, and said anvils of said first and second nests disposed toward each other.

6. The combination of claim 5 wherein said holder includes a channel on said upper surface of said holder, said nests being mounted in said channel, and a wafer movably mounted for movement through the space between said anvils.

7. The combination of claim 6 wherein said tube receiving areas comprise grooves in said upper surface of said block to define curved walls for receiving said sections of said tube.

8. The combination of claim 6 wherein a pin extends downwardly from each of said blocks, said pin having a peripheral groove, said channel having a hole for each of said pins, each of said holes having an O-ring, and said O-ring being mounted to said peripheral groove of its respective pin when its respective nest is mounted in said channel.

9. The combination of claim 6 including a fixed clamp arm mounted in said channel adjacent one of said tube receiving areas of each of said nests, a pivoted clamp arm mounted in said channel adjacent the other of said tube receiving areas of each of said nests, and each of said nests being pivotally mounted in said channel.

10. The combination of claim 9 including a wedge slidably mounted for movement between each of said pivoted clamp arms and the channel wall to cause said clamp arm to move to a closed position and to cause said clamp arm to pivot said nest to a straight position.

11. The combination of claim 10 wherein each of said clamp arms terminates in a curved end.

12. The nest of claim 3 wherein said locking member comprises a pin having a peripheral groove, and said anvil is made of a meltable plastic material.

13. The nest of claim 2 including a pair of pivotally mounted clamp arms on said block with each of said clamp arms being disposed at a respective one of said tube receiving areas.

14. The nest of claim 13 including a locking post for each of said clamp arms mounted on said upper surface of said block, each of said locking posts and its respective arm having complementary locking means for mounting said arm to said locking post when said arm is in its clamped position.

15. The nest of claim 14, in combination therewith, a holder, said holder having an upper surface, a channel extending across said upper surface of said holder, said nest comprising a first nest mounted in said channel, a second nest mounted in said channel adjacent said first nest, said second nest having an anvil, said anvils of said nests disposed toward each other, and a wafer movably mounted in said holder through the space between said anvils.

16. The nest of claim 2 including a fixed clamp on one side of said partition, a hinged clamp on the side of said partition opposite said fixed clamp, and said hinged clamp being movable to an open position which is at least in line with said fixed clamp so that both of said tube receiving areas are readily accessible.

17. The nest of claim 16 wherein said hinged clamp is mounted to said block by a flexible hinge, and said flexible hinge permitting said hinged clamp to be pivoted beyond the in line position of said fixed clamp.

18. The nest of claim 17, in combination therewith, a holder, said holder having an upper surface, a channel extending across said upper surface of said holder, said nest comprising a first nest mounted in said channel, a second nest mounted in said channel adjacent said first nest, said second nest having an anvil, said anvils of said nests disposed toward each other, and a wafer movably mounted in said holder through the space between said anvils.

19. The combination of claim 5 wherein one of said anvils is thicker than other of said anvils whereby one tube section in one of said nests would be aligned with a corresponding tube section in the other of said nests and another of said tube sections would be misaligned with but positioned to contact a corresponding tube section in the other of said nests.

20. A method of welding sections from two plastic tubes comprising the steps of bending one of the tubes around an anvil of a nest having two side by side tube receiving areas, locating the sections of the tube adjacent the bent portion in the tube receiving areas, repeating the bending and locating steps with the other of the tubes around a second anvil of a second nest, clamping the tubes in the nests, mounting the nests on a support surface with the bent portions of the tubes disposed toward each other, passing a heater wafer through the area where the bent portions of the tubes are disposed toward each other to contact and melt the bent portions, and welding a tube section from each tube with a corresponding tube section of the other tube.

21. The method of claim 20 including mounting each nest to a holder having a wafer which is movable through the space between the anvils of the nests.

22. The method of claim 21 wherein each of said nests is permanently mounted to the holder.

23. The method of claim 21 including mounting each nest in a channel in the upper surface of the holder.

24. The method of claim 23 including detachably mounting each nest in the channel.

25. The method of claim 24 wherein each nest includes at least one pin extending downwardly from the nest with a peripheral groove in the pin and including the step of snapping the pin into a corresponding hole in the channel with an O-ring in the hole being snapped into the peripheral groove.

26. The method of claim 24 including removing at least one of the tubes and its nest from a sealed packet with the tube mounted to the nest before the tube and nest assembly is mounted in the channel.

27. The method of claim 24 wherein each nest includes a partition having a fixed clamp on one side and a pivoted clamp on the other side and including the steps of pivotally mounting each nest in the channel, pivoting each clamp and its nest away from its fixed clamp, inserting one tube section in a tube receiving area adjacent the fixed clamp, bending the tube around the anvil inserting an adjacent tube section in the area adjacent the pivoted clamp, and pivoting the clamp and its nest toward the fixed clamp.

28. The method of claim 27 including sliding a wedge against the pivoted clamp and a wall of the channel to pivot the clamp to a closed position and the pivoting action of the clamp causing the clamp to press against the nest to pivot the nest to its straight position.

29. The method of claim 28 wherein each of the clamps terminates in a curved end and flattening each tube section between the curved end and pointed end of the anvil.

30. The method of claim 24 wherein each nest has a pair of pivoted clamp arm on each side of a partition in the nest separating the tube receiving areas and including the steps of pivoting each clamp arm away from its tube receiving area to expose the tube receiving area and permit the insertion of a tube section therein, and moving each pivoting clamp arm to a locked position after each tube section has been inserted in its tube receiving area.

31. The method of claim 30 including joining two sets of tube sections together as a result of the welding step, the two sets of tube sections being connected to each other by a web flange, inserting the joined sets in a nest with one set in a tube receiving area and the other set disposed above that set, and closing the respective clamp arm to break the flange and separate the two sets from each other.

32. The method of claim 30 including inserting a welded tube section in a tube receiving area, closing the clamp arm to press against the welded tube section and open communication therein by means of the clamp arm acting as a pliers.

33. The method of claim 24 wherein each of the nests includes a partition between the two tube receiving areas with a fixed clamp on one side of the partition and a hinged clamp on the other side of the partition including the steps of pivoting the hinged clamp away from its tube receiving area to a position at least in line with the fixed clamp to completely expose both tube receiving areas of the nest, inserting a tube section in each tube receiving area when the tube receiving areas are completely exposed, and closing the clamp after the tube sections have been inserted in their tube receiving areas.

34. The method of claim 20 wherein a set of two nests is provided on each side of a process container with a tube extending from each side of the process container to a respective one of the nests including the steps of joining a tube from each of the sets as a result of the welding steps to create an assembly of welded tube sections which permits the flow of fluid from one side of the process container through the process container and to the other side, and mixing a substance from the process container with the fluid flowing from the tubes and through the process container.

35. The method of claim 20 including providing one tube from a main source and another tube from a sample container wherein the method is used for taking a sample from the main source and discharging it into the sample container including the steps of creating a welded main tube as a result of the welding step with the main tube extending from the source to the sample container, and filling the sample container with fluid flowing from the main source through the main tube and into the sample container.

36. The method of claim 35 including creating a stub tube from welded sections of the tubes as a result of the welding step, closing the system which comprises the main source and the sample container by welding a section of the stub tube to a section of the welded tube to create two new tubes, and sealing each end of the new tubes.

37. The method of claim 36 wherein after the new tubes have been closed, a further sample is taken by repeating the sample taking steps.

38. The method of claim 36 wherein the method is used for taking a new sample by repeating the sample taking steps before the closing steps.

39. The method of claim 20 wherein the method is used for CAPD bag installation wherein the patient is provided with a tube and a first bag is provided with a different tube and including the steps of connecting the two tubes together by the welding step to create a new main tube leading from the patient to the first bag and a stub tube resulting from additional tube sections of the two tubes.

40. The method of claim 39 wherein the method is used for replacing the first bag with a second bag having a tube and including the steps of using the welding step to form a new main tube which leads from the patient to a section of the second bag with a tube section being connected to the first bag.

41. The method of claim 20 wherein the method is used to remove a tube section containing a consummable container wherein the consummable container has a tube leading from each side to a pair of main sources and including the steps of bending each tube to create a new main tube which joins the two main sources and leaving a closed loop tube connected to the consummable container.

42. The method of claim 20 wherein the method is used to install a consummable container and wherein a main source is provided which provides a tube connected at both ends to the main source with the consummable container having a closed loop tube connected at each end to the consummable container and including the steps of inserting each of the tubes in a nest and using the welding step to form a first tube leading from the main source to the consummable container and a second tube leading from the consummable container back to the main source.

43. The method of claim 20 wherein the method is used for forming a loop from a tube which joins one flow system to another flow system and including the steps of bending portions of the tube around a respective anvil of two nests, aligning a section of one tube portion in one nest with a corresponding tube portion in the other nest, welding the aligned sections together to create a loop, and connecting the remaining systems to each other by the other tube sections.

44. The method of claim 43 including misaligning a different tube section in one nest with a corresponding tube section in the other nest wherein the tube sections are misaligned but disposed to contact each other, and sealing the misaligned tube sections as a result of the weld that occurs when the misaligned sections are welded together.

45. A method of forming a weld seal from two distal tube ends which are closed including the steps of mounting the closed tube ends in co-axial mounting blocks, clamping and flattening the tube ends, moving a heater between the tube ends, contacting the heater and both tube ends while the heater is moving to weld the tube ends to each other in a melt-wipe operation in which after the tube ends are melted the tube ends are pressed together to form a single tube, and re-opening the joined tube ends of the single tube.

* * * * *